(12) United States Patent
Karl et al.

(10) Patent No.: US 9,288,978 B2
(45) Date of Patent: Mar. 22, 2016

(54) INSECTICIDE-IMPREGNATED NETS AND USE THEREOF FOR PROTECTING AGAINST PESTS

(75) Inventors: Ulrich Karl, Grünstadt (DE); Susanne Stutz, Weinheim (DE); Hartmut Leininger, Neustadt (DE); Claus Kaiser, Mannheim (DE)

(73) Assignee: BASF SE, Ludwigshafen (DE)

( * ) Notice: Subject to any disclaimer, the term of this patent is extended or adjusted under 35 U.S.C. 154(b) by 248 days.

(21) Appl. No.: 13/055,555

(22) PCT Filed: Jul. 27, 2009

(86) PCT No.: PCT/EP2009/059626
§ 371 (c)(1),
(2), (4) Date: Jan. 24, 2011

(87) PCT Pub. No.: WO2010/012671
PCT Pub. Date: Feb. 4, 2010

(65) Prior Publication Data
US 2011/0120001 A1 May 26, 2011

(30) Foreign Application Priority Data
Jul. 30, 2008 (EP) .................................... 08161456

(51) Int. Cl.
*A01G 13/02* (2006.01)
*A01N 25/34* (2006.01)

(52) U.S. Cl.
CPC ........... *A01N 25/34* (2013.01); *Y10T 29/49826* (2015.01)

(58) Field of Classification Search
USPC ........................................................ 47/32.3
See application file for complete search history.

(56) References Cited

U.S. PATENT DOCUMENTS

| | | | | |
|---|---|---|---|---|
| 2,353,224 A * | 7/1944 | Dreyfus | ........................ | 442/43 |
| 3,301,740 A * | 1/1967 | Stiehl et al. | ................... | 428/156 |
| 5,097,624 A * | 3/1992 | Klayman et al. | .................. | 47/31 |
| 6,796,083 B2 * | 9/2004 | Hadar | ............................. | 47/31 |
| 8,215,051 B2 * | 7/2012 | Alexander et al. | ........... | 43/132.1 |
| 2002/0020110 A1 | 2/2002 | Klayman | | |
| 2005/0019364 A1 * | 1/2005 | Frandsen et al. | .............. | 424/411 |
| 2008/0200604 A1 | 8/2008 | Fechtenkotter et al. | | |
| 2009/0246242 A1 * | 10/2009 | Leininger et al. | ............. | 424/411 |
| 2010/0064578 A1 * | 3/2010 | Karl et al. | ......................... | 47/31 |
| 2012/0114726 A1 * | 5/2012 | Leininger et al. | ............. | 424/411 |
| 2012/0114727 A1 * | 5/2012 | Leininger et al. | ............. | 424/411 |

FOREIGN PATENT DOCUMENTS

| | | |
|---|---|---|
| EP | 1411764 A1 | 4/2004 |
| JP | S6136487 A | 2/1986 |
| JP | H02160537 A | 6/1990 |

(Continued)

OTHER PUBLICATIONS

JP 2002176863 translation; retrieved from JPO website Feb. 8, 2013.*
JP2000217497 translation; retrieved from JPO website Feb. 8, 2013.*
JP2000166399 translation; retrieved from JPO website Feb. 8, 2013.*

(Continued)

*Primary Examiner* — Kristen C Hayes
(74) *Attorney, Agent, or Firm* — Drinker Biddle & Reath LLP

(57) ABSTRACT

Insecticide-impregnated nets made of textile fibers, which nets have a small mesh size, and their use for the protection against pests.

4 Claims, 3 Drawing Sheets

(56) References Cited

FOREIGN PATENT DOCUMENTS

| | | | | |
|---|---|---|---|---|
| JP | 2-270803 A | | 11/1990 | |
| JP | 7289097 | * | 11/1995 | |
| JP | 2000166399 | * | 6/2000 | |
| JP | 2000217497 | * | 8/2000 | |
| JP | 2000217497 A | * | 8/2000 | ............ A01M 29/00 |
| JP | 2001-292688 A | | 10/2001 | |
| JP | 2002176863 | * | 6/2002 | |
| JP | 2006180759 A | | 7/2006 | |
| SU | 544742 | | 8/1975 | |
| WO | WO-02/46503 A1 | | 6/2002 | |
| WO | WO-03/034823 A1 | | 5/2003 | |
| WO | WO2003/090532 | | 6/2003 | |
| WO | WO-2005/064072 A2 | | 7/2005 | |
| WO | WO-2006/128870 A2 | | 12/2006 | |
| WO | WO-2007/009909 A1 | | 1/2007 | |
| WO | WO-2007/077101 A1 | | 7/2007 | |
| WO | WO-2007/144401 A2 | | 12/2007 | |
| WO | WO 2007144401 A2 | * | 12/2007 | |
| WO | WO-2008/004711 A2 | | 1/2008 | |
| WO | WO-2008/052913 A1 | | 5/2008 | |
| WO | WO-2008/151984 A1 | | 12/2008 | |
| WO | WO 2010016561 A2 | * | 2/2010 | ............ A01N 25/34 |

OTHER PUBLICATIONS

JP7289097 translation; retrieved from JPO website Feb. 8, 2013.*
JP 2002176863 abstract; retrieved from EPO website Feb. 8, 2013.*
JP2000217497 abstract; retrieved from EPO website Feb. 8, 2013.*
Jp 2000166399 abstract; retrieved from EPO website Feb. 8, 2013.*
Jp 7289097 abstract; retrieved from EPO website Feb. 8, 2013.*
Bethke, J., et al., "Screen hole size and barriers for exclusion of insect pests of Glasshouse Crops", J. Entomol. Sc., vol. 26, No. 1, (1991), pp. 169-177.
International Search Report for PCT/EP2009/059626, dated Dec. 7, 2010.
"Nzitrap Mesh Sizes for Netting", webpage, obtained from http://www.nzitrap.com/Nzi_trap/Fabrics/Mesh_Sizes.htm, (updated 2007), as recited by the Russian Office on Jan. 28, 2013.
U.S. Appl. No. 12/513,173, filed May 1, 2009, Ulrich, et al.
U.S. Appl. No. 12/664,197, filed Dec. 11, 2009, Ulrich, et al.
U.S. Appl. No. 12/671, 613, filed Feb. 1, 2010, Leininger.
International Preliminary Report on Patentability issued in related International Application No. PCT/EP2009/059626 on Feb. 1, 2011.
English-language translation of the International Preliminary Report on Patentability issued in related International Application No. PCT/EP2009/059626 on Mar. 15, 2011.

* cited by examiner

INSECTICIDE-IMPREGNATED NETS AND USE THEREOF FOR PROTECTING AGAINST PESTS

CROSS-REFERENCE TO RELATED APPLICATIONS

This application is a national stage application (under 35 U.S.C. §371) of PCT/EP2009/059626, filed Jul. 27, 2009, which claims benefit of European application 08161456.2, filed Jul. 30, 2008.

BACKGROUND OF THE INVENTION

The invention relates to insecticide-impregnated nets made of textile fibers, which nets have a small mesh size, and their use for the protection against pests.

Insect protection nets are known in principle. For example, they are used as windows in order to keep all sorts of insects as well as larger animals such as birds or rodents out of the house. Another example which may be mentioned is the use of mosquito nets. Insect protection nets are furthermore used for protecting plants, plant parts, fruits or non-living materials from pests, for example by wrapping the plants or materials to be protected in them, or by using the nets as windows in greenhouses or for the construction of greenhouses.

Insect protection nets are commercially available with different mesh sizes. Typical mosquito nets made of polyester have meshes with a size of approximately 2 mm×2 mm; commercially available mosquito nets made of polyethylene monofilament frequently have hexagonal meshes, the distances between the parallel sides being 2.5 mm.

However, small insects such as, for example, thrips, whiteflies or sand flies, are still capable of passing through nets with such a mesh size. In "Screen hole size and barriers for exclusion of insect pests of glasshouse crops" J. Entomol. Sc. 26: 169-177 (1991), Bethke et al. specify a "critical insect diameter" of approximately 0.2 to approximately 0.6 mm for a variety of relatively small insects. Nets through which even the above insects should no longer be able to pass must, therefore, have considerably smaller mesh sizes than customary mosquito nets. Commercially available nets for protection against such insects have mesh sizes of less than 1 mm×1 mm down to 0.15 mm×0.15 mm.

However, it is a disadvantage that the permeability of the net to air, water vapor and light also decreases with decreasing mesh size. Thus, the permeability to air of very close-meshed nets may frequently be reduced by approximately 50% in comparison with wide-meshed nets. This decrease in permeability is highly undesirable for many applications of the nets, in particular when used as window materials for greenhouses; rather, a sufficient air exchange and the diffusion of water vapor should be possible, and, also, the light intensity must not be unduly reduced.

It is furthermore known to impregnate insect protection nets, in particular mosquito nets, with insecticides.

WO 2003/034823 discloses a formulation for impregnating mosquito nets and nets impregnated therewith, which formulation comprises at least one insecticide, a copolymeric binder and at least one dispersant.

WO 2005/064072 discloses a formulation for impregnating mosquito nets and nets impregnated therewith, which formulation comprises at least one insecticide or other active ingredient and at least one binder. The binder may take the form of a polyacrylate which comprises, as monomers, at least n-butyl acrylate, an acrylate which differs therefrom, and at least one hydroxyalkylacrylamide.

EP 1 411 764 B1 discloses fences for preventing the penetration of low-flying insects into certain zones in the open, which fences comprise insecticide-impregnated nets.

WO 2007/144401 discloses a method for protecting tobacco, where the tobacco is covered with an insecticide-impregnated material, for example an insecticide-impregnated net. The examples disclose nets with square meshes 2 mm×2 mm or 1 mm×1 mm in size.

WO 2008/52913 discloses a method of protecting useful plants, where the plants are covered with a pesticide-impregnated net which is permeable to light, air and water.

JP 2270803 A discloses a net for protection against insects, the threads of which are obtained by melting together an ethylene/vinyl acetate copolymer and the active ingredient empenthrin and optional further active ingredients. The threads may have a diameter of from 0.2 to 1 mm, and the mesh size is 2 to 4 mm.

JP 2001-292688 A discloses an insect protection net for fitting into windows of dwellings, offices and greenhouses, which insect protection net is made of polyolefin fibers and is coated with an acrylic resin. The mesh density is 20×20 threads per direction and inch; this corresponds to a mesh size of approx. 1.5 mm². However, the net is not impregnated with insecticides.

WO 2008/004711 discloses a net for controlling insects, the fibers of which net have a thermoplastic polymer and an active ingredient with a vapor pressure $<1*10^{-6}$ mm Hg at 25° C., and the net having essentially identical meshes with an area of in each case 2 mm² up to 36 mm².

BRIEF SUMMARY OF THE INVENTION

It was an object of the invention to provide nets for the protection of humans, animals, plants and non-living materials against attack by pests, which nets offer sufficient protection even from small insects while having good permeability to air, water vapor and light. The nets are intended in particular for protection against sand flies and to be suitable for the construction of greenhouses and the protection of window, door and ventilation openings.

Surprisingly, it has been found that this problem can be solved by finishing fine-meshed nets with insecticides. The finished fine-meshed nets offer adequate protection even under comparatively high population pressure. More particularly, they still offer protection when the net has minor damage, such as holes for example.

Accordingly, there have been found insect protection nets made of textile fibers with a thickness of 0.05 mm to 0.6 mm, the textile fibers being arranged in such a way that the net comprises a pattern of meshes with an even number of corners, and the net being finished with at least one insecticide, and the meshes being selected from the group consisting of tetragonal meshes in the form of a parallelogram with the sides a and b and a height $h_a$, the height $h_a$ being from 0.1 mm to 0.99 mm and the length/height ratio $b/h_a$ being 1:1 to 5:1, and hexagonal meshes, which have three pairs of sides a, b and c which are in each case parallel to one another spaced apart by the distances $h_a$, $h_b$ and $h_c$, the height $h_a$ being from 0.1 to 0.99 mm and the ratio $((h_b+h_c)/2)/h_a$ being 1:1 to 5:1, octagonal meshes, which have four pairs of sides a, b, c and d which are in each case parallel to one another spaced apart by the distances $h_a$, $h_b$, $h_c$ and $h_d$, the height $h_a$ being from 0.1 to 0.99 mm and the ratio $((h_b+h_c+h_d)/3)/h_a$ being 1:1 to 5:1, and the specifications of length and height referring in each case to the dimensions of the mesh.

BRIEF DESCRIPTION OF THE DRAWINGS

FIG. 2 shows a likewise diagrammatic representation of the definition of the variables a, b, c and $h_a$, $h_b$ and $h_c$.

FIG. 3 shows a likewise diagrammatic representation of the definition of the variables a, b, c, d and $h_a$, $h_b$, $h_c$ and $h_d$.

DETAILED DESCRIPTION OF THE INVENTION

Figure 1:
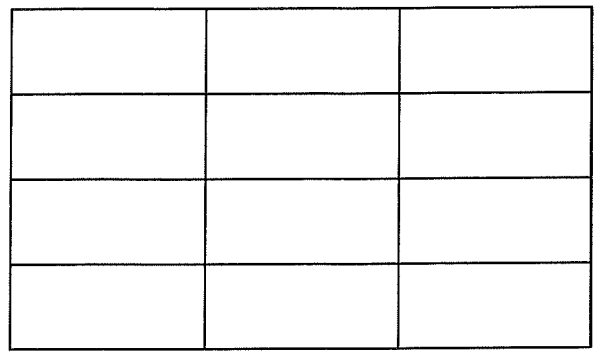
FIG. 1 illustrates the construction of two nets made of parallelograms. Moreover, FIG. 1 gives a likewise diagrammatic representation of the definition of the variables a, b and $h_a$.
Figure 1:
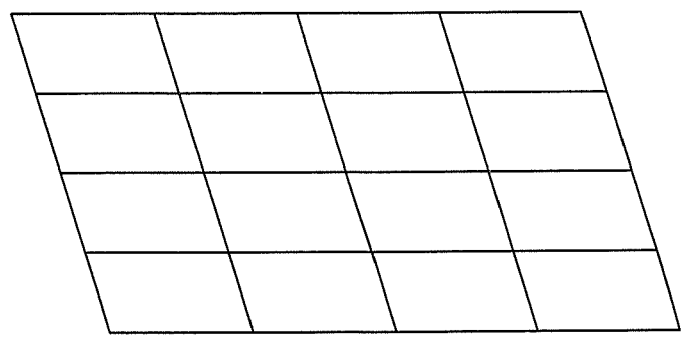
Figure 1:
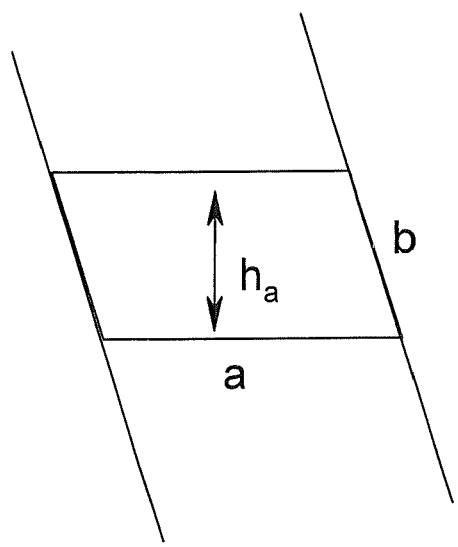

In a preferred embodiment of the invention the net is impregnated with a preferably aqueous formulation which comprises at least one insecticide and at least one polymeric binder.

The invention further provides for the use of such nets for the protection of window and door openings, for the construction of greenhouses, for the protection of plants and for the protection of goods, particularly tea, tobacco or cotton.

What follows now is a description of the details of the invention.

Nets

The nets are nets made of textile fibers. They may take the form of nets made of natural fibers or else synthetic fibers. Naturally, the fibers may also be mixtures of two or more different fibers. Examples of natural fibers comprise cotton, jute or flax fibers. The fibers are preferably synthetic fibers made of suitable polymers. Examples comprise polyamides, polyesters, polyacrylonitrile or polyolefins. They are preferably polyamides, polyolefins and polyesters, especially preferably polyolefins or polyesters, in particular PET, and very especially preferably polyolefin fibers, in particular polypropylene or polyethylene.

They may take the form of smooth or textured fibers. The fibers may be mono-, oligo- or multifilaments.

Polypropylene and polyethylene may take the form of polypropylene homopolymers or polyethylene homopolymers. However, they may also take the form of copolymers which, besides the ethylene or propylene, comprise small amounts of other comonomers. Suitable comonomers may be in particular other olefins such as, for example, ethylene or propylene and also but-1-ene, but-2-ene, isobutene, pent-1-ene, hex-1-ene, hept-1-ene, oct-1-ene, styrene or α-methylstyrene, dienes and/or polyenes. The comonomers in the polyethylene or polypropylene generally amount to no more than 20% by weight, preferably no more than 10% by weight. The nature and amount of comonomers are selected by the skilled worker to match the desired properties of the fiber.

Viscous products with a relatively high molecular weight, which are characterized in a customary manner by their melt flow index (determined as specified in ISO 1133), are especially preferred for the production of fibers. This product can preferably take the form of at least one polypropylene or polyethylene with a melt flow index MFR (230° C., 2.16 kg) of from 0.1 to 60 g/10 min. They preferably take the form of polypropylene with a melt flow index MFR (230° C., 2.16 kg) of from 1 to 50 g/10 min, especially preferably 10 to 45 g/10 min and for example 30 to 40 g/10 min. Such types of polypropylene are particularly suitable for the production of fibers. Naturally, a mixture of a plurality of different types of polypropylene may also be employed.

Depending on the nature of the net, the textile fibers of the net have a thickness of from 0.05 to 0.6 mm, preferably from 0.1 mm to 0.4 mm, especially preferably from 0.12 to 0.35 mm and very especially preferably from 0.2 to 0.3 mm.

The textile fibers are arranged in the form of a net, the net having a pattern of meshes with an even number of corners. In this context, the nets may preferably only consist of a single type of mesh, for example only of tetragonal or only of hexagonal meshes, or else they may comprise two or more types of different meshes, for example a combination of octagonal and tetragonal meshes.

In this context, the meshes of the net should preferably be essentially identical, i.e. while the net may indeed have minor deviations as regards shape and size of the meshes, the values will not vary excessively around the mean.

The meshes of the net are preferably selected from the group of tetragonal, hexagonal or octagonal meshes.

The tetragonal meshes take the form of meshes in the form of a parallelogram with the sides a and b. The term "parallelogram" naturally also comprises the terms "rectangle" and "square". The smaller angle between the two sides of the parallelogram will, as a rule, be between 60 and 90°. In the borderline case of 90°, the parallelogram takes the form of a rectangle. In the borderline case a=b and 90°, it takes the form of a square. Furthermore, the parallelogram has the height $h_a$. In a rectangle or square, the height $h_a$ corresponds to the length of side a.

The construction of two nets made of parallelograms is shown diagrammatically in FIG. 1. Moreover, FIG. 1 gives a likewise diagrammatic representation of the definition of the variables a, b and $h_a$.

In the case of the hexagonal meshes, three pairs of sides a, b and c which are in each case parallel to one another are arranged spaced apart by the distances $h_a$, $h_b$ and $h_c$.

Figure 2:
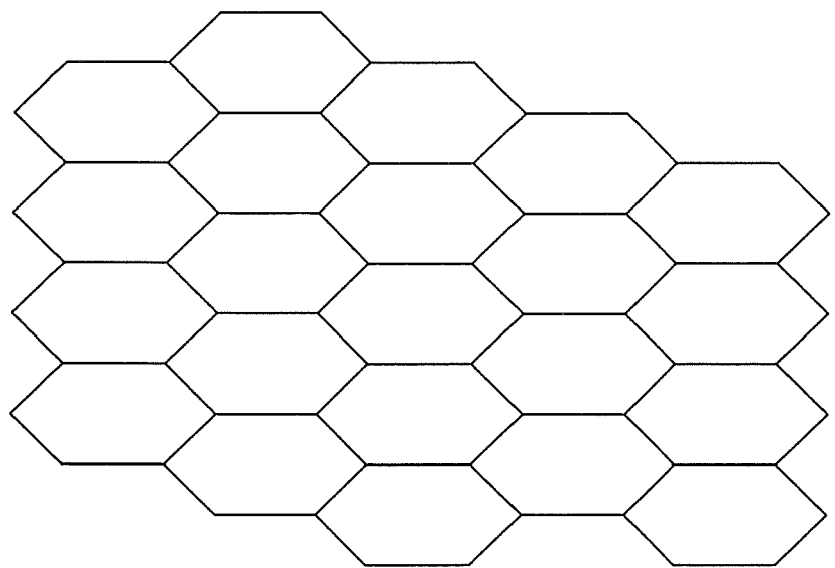
FIG. 2 illustrates the construction of a net made of hexagons. Furthermore.
Figure 2:
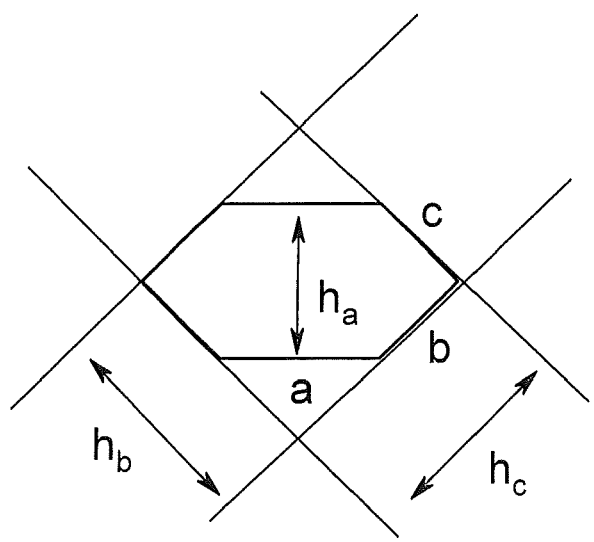

The construction of a net made of hexagons is shown diagrammatically in FIG. 2. Furthermore, FIG. 2 shows a likewise diagrammatic representation of the definition of the variables a, b, c and $h_a$, $h_b$ and $h_c$.

Figure 3:
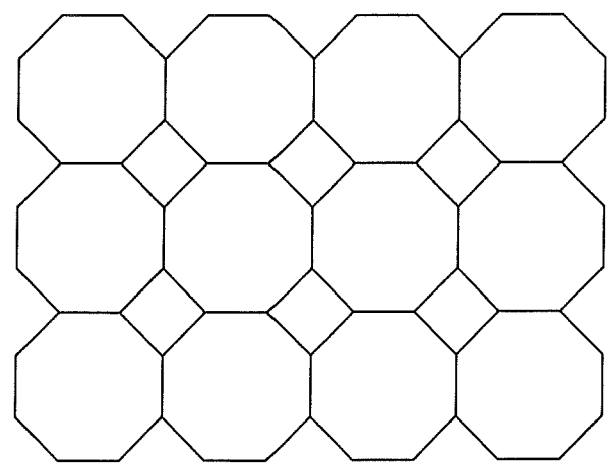
FIG. 3 illustrates the construction of a net made of octagons. Furthermore.
Figure 3:
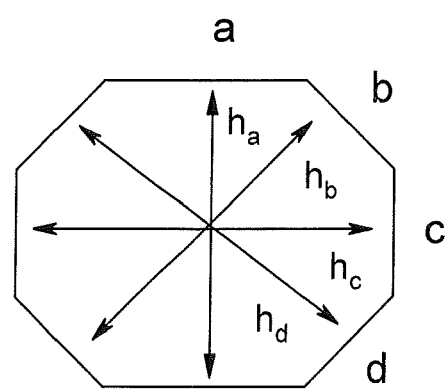

In the case of the octagonal meshes, four pairs of sides a, b, c and d which are in each case parallel to one another are arranged spaced apart by the distances $h_a$, $h_b$, $h_c$ and $h_d$. The construction of a net made of octagons is shown diagrammatically in FIG. 3. Furthermore, FIG. 3 shows a likewise diagrammatic representation of the definition of the variables a, b, c, d and $h_a$, $h_b$, $h_c$ and $h_d$. The skilled worker knows that no continuous sheet-like pattern may be formed using octagons. A net which comprises octagonal meshes will therefore additionally comprise at least one second type of mesh. This may take the form of tetragonal meshes as shown for example in FIG. 3.

In accordance with the invention, the height $h_a$ in the parallelogram, the hexagon and the octagon is in each case from 0.1 to 0.99 mm, preferably from 0.1 to 0.9 mm, especially preferably from 0.12 to 0.8 mm and very especially preferably from 0.25 to 0.7 mm.

In the case of the parallelogram, the length/height ratio $b/h_a$ is 1:1 to 5:1, preferably 1:1 to 4:1 and especially preferably 2:1 to 4:1. That is to say that in the case of a $b/h_a$ ratio of 1:1, the meshes may take the form of a square with a side length of from 0.1 to 0.99 mm. In the case of a greater $b/h_a$ ratio, a shape which extends longitudinally in one direction is obtained. As a result of the distance $h_a$ of no more than 0.99 mm, even relatively small insects are efficiently prevented from passing through the net, while the length may indeed be greater than 0.99 mm so that the permeability of the net to air will not be unduly affected.

In the case of the hexagon, the ratio $((h_b+h_c)/2)/h_a$ is from 1:1 to 5:1, preferably 1:1 to 4:1 and especially preferably 2:1 to 4:1. Here, the ratios are analogous to the parallelogram. In the case of a ratio of 1:1, a regular hexagon with three equal sides is obtained, which sides are in each case spaced apart from one another by the same distance of no more than 0.99 mm. In the case of a greater ratio $((h_b+h_c)/2)/h_a$, a hexagon which extends longitudinally in one direction is obtained. The efficacy as regards permeability to insects and air is as for the parallelogram.

In the case of the octagon, the ratio $((h_b+h_c+h_d)/3)/h_a$ is from 1:1 to 5:1, preferably 1:1 to 4:1 and especially preferably 2:1 to 4:1. Here, the ratios are analogous to the parallelogram. In the case of a ratio of 1:1, a regular octagon with four equal sides is obtained, which sides are in each case spaced apart from one another by the same distance of no more than 0.99 mm. In the case of a greater ratio $((h_b+h_c)/3)/h_a$, an octagon which extends longitudinally in one direction is obtained. The efficacy as regards permeability to insects and air is as for the parallelogram.

Besides tetragonal and hexagonal meshes, it is also possible to employ for example combinations of tetragonal and octagonal meshes, or to vary the shape and size of the meshes in parts of the net. For example, the edges of the net can be knitted to be denser, or thicker textile fibers, which may also be made from another polymer, may be knitted in at intervals in order to stabilize the net.

The terms "height" and "length" refer to the open area of each mesh without taking into consideration the fibers, or the coated fibers. Analogously, the term "mesh size" means, for the purposes of the present invention, the hole size of the meshes, i.e. the open area of each mesh without taking into consideration the fibers or the coated fibers.

The thickness of the fibers used for the production of the nets is selected by the skilled worker depending on the desired properties of the net. As a rule, the thicker the fibers, the greater the mechanical stability of the net; on the other hand, the proportion of open area in comparison with the proportion of the fiber-covered area will decrease with decreasing mesh size. As a rule, the fiber thickness should be such that the open area of the net will be at least 20%, preferably at least 40% and in particular at least 50% of the net. Nets of the abovementioned type are commercially available.

The nets used can preferably take the form of single-layer nets. However, they may also take the form of what are known as spacer fabrics, where two nets are connected to one another with the aid of individual yarns to form a double layer.

Insecticides

According to the invention, the nets are provided with at least one insecticide. The active ingredient used may, in principle, be any insecticide. This term is also intended to comprise those insecticides which, while not destroying insects, have a repellent effect on insects. Depending on the nature of the intended use, the skilled worker makes a suitable selection. Naturally, it is also possible to use mixtures of a variety of insecticides. Furthermore, it is also possible to use combinations of insecticides with metabolic inhibitors, also known as efficiency boosters, such as, for example, piperonyl butoxide (PBO).

Insecticides which are suitable for carrying out the invention are mentioned for example in WO 2005/64072, page 11, line 28 to page 14, line 34. Further examples include N-arylhydrazines as mentioned in WO 2006/128870, page 12, line 1 to page 18, line 37.

Preferably, this is at least one insecticide or insect repellent selected from the group of synthetic or natural pyrethroids such as, for example, alpha-cypermethrin, cyfluthrin, deltamethrin, ethofenprox, permethrin or bifenthrin, chlorfenapyr and fipronil. Alpha-cypermethrin and chlorfenapyr are especially preferred.

Finishing the Nets with Insecticides

In the case of thermoplastic textile fibers, the insecticides used can be directly incorporated in the fibers by adding the insecticides to the polymer melt used for spinning the fibers. This can be effected for example during the customary melt extrusion before spinning.

A further embodiment of the invention utilizes nonimpregnated nets of textile fibers which are impregnated with at least one insecticide. The insecticides may preferably be fixed on the fiber by means of suitable low molecular weight or polymeric auxiliaries.

Preferably, the nonimpregnated nets may be impregnated with a mixture comprising at least one insecticide and at least one polymeric binder. The treatment is carried out particularly preferably with an aqueous formulation comprising at least one insecticide and at least one polymeric binder.

Polymeric Binders

The binder serves to fix the insecticide to the net. What is achieved hereby is that the active ingredient can be leached out not at all or at least only very slowly. Insect protection nets are frequently exposed to water, in particular to natural precipitation, as the result of dew formation or else due to artificial irrigation.

The polymeric binder may, in principle, take the form of any binder with the proviso that the binders are capable of fixing insecticides to textile materials. Binders which are particularly preferred are those known from the field of textile finishing and textile coating. Naturally, it is also possible to employ a mixture of a plurality of different binders.

Examples include homo- or copolymers comprising (meth)acrylates, or polyurethanes, polyisocyanurates or waxes, in particular polyethylene waxes. Suitable binders are disclosed for example in WO 2005/064072 on pages 17 to 24 or WO 2008/052913 on pages 21 to 33.

For example, they may be binders which can be obtained by polymerization of ethylenically unsaturated monomers, preferably at least one monomer selected from the group consisting of (meth)acrylates, in particular $C_1$- to $C_{12}$-esters of (meth)acrylic acid, (meth)acrylates having crosslinking groups, (meth)acrylic acid, maleic acid or maleic acid esters, acrylonitrile, styrene, vinyl acetate, vinyl alcohol, ethylene, propylene, allyl alcohol or vinyl chloride.

In a preferred embodiment of the invention, this is a copolymer I of ethylenically unsaturated monomers which comprises, as monomers, 50 to 95% by weight of at least one (meth)acrylate (A) of the general formula $H_2C{=}CHR^1{-}COOR^2$, where $R^1$ is H or methyl and $R^2$ is an aliphatic, linear or branched hydrocarbon radical having 1 to 12 carbon atoms, preferably 2 to 10 carbon atoms. $R^1$ is preferably H. Examples of suitable radicals $R^2$ include in particular methyl, ethyl, n-butyl or 2-ethylhexyl radicals, preferably ethyl, n-butyl or 2-ethylhexyl radicals. Moreover, the copolymer I comprises 1 to 20% by weight of (meth)acrylic acid or (meth)acrylic acid derivatives (B) with additional functional groups. This may take the form in particular of a (meth)acrylic ester and/or (meth)acrylamides. The functional groups serve to bind the binder to the nets and can furthermore be used for crosslinking. For example, they may take the form of ω-hydroxyalkyl (meth)acrylic esters, (meth)acrylic esters having epoxy groups such as, for example, glycidyl esters, (meth)acrylamides or derivatives thereof such as, for example, (meth)

acrylic acid methylolamide $H_2C=CH(CH_3)—CO—HN—CH_2—OH$. It is at the same time also possible to employ further ethylenically unsaturated, preferably monoethylenically unsaturated, monomers (C) which differ from A and B, for example acrylonitrile or styrene. As a rule, the amount of further monomers is from 0 to 30% by weight. Further details on the copolymers I are described in WO 2008/052913 page 24, line 3 to page 27, line 32. Very especially preferred binders are described in WO 2008/052913 page 28, line 11 to page 30, line 6. Especially preferred is a binder which comprises 70 to 90% by weight of an acrylic ester of the formula $H_2C=CH_2—COOR^2$, where $R^2$ comprises 4 to 8 C atoms and which is preferably n-butyl and/or 2-ethylhexyl, and furthermore 10 to 20% by weight of acrylonitrile, 1 to 10% by weight of (meth)acrylic acid or a (meth)acrylic acid derivative which has functional groups, in particular (meth)acrylic acid methylolamide.

The abovementioned preferred binders can preferably be employed by means of emulsion polymerization. Details in this context are described in WO 2005/064072 page 20, line 20 to page 23, line 15.

In a further preferred embodiment of the invention, the binder is a copolymer II which is composed of 60 to 95% by weight of ethylene, 5 to 40% by weight of at least one ethylenically unsaturated carboxylic acid selected from the group of $C_3$- to $C_{10}$-monocarboxylic acids and $C_4$- to $C_{10}$-dicarboxylic acids and optionally 0 to 30% by weight of further monomers. Examples of carboxylic acids comprise (meth)acrylic acid, maleic acid or fumaric acid. (Meth)acrylic acid is preferred. Further monomers may for example be other olefins such as propene, 1-butene, (meth)acrylates such as methyl(meth)acrylate, ethyl(meth)acrylate, n-butyl(meth)acrylate or vinylphosphonic acid.

Details regarding the preparation of such copolymers II are disclosed for example in WO 2007/009909. Further details regarding this preferred class of binder are disclosed in PCT/EP2008/057048.

Impregnating Formulation—Crosslinkers

To prepare the nets according to the invention, the binders may be employed in the form of a formulation in a solvent, preferably as an aqueous formulation; however, the invention also comprises the use of solvent-free formulations.

In a preferred embodiment of the invention, aqueous formulations are employed which comprise 55 to 99% by weight of water, preferably 85 to 98% by weight of water and 1 to 45% by weight, preferably 2 to 15% by weight, of solids, the quantities given being in each case based on the total of all components in the formulation. The precise concentration also depends on the adsorptivity of the textile substrate.

The solids take the form of at least one binder, at least one insecticide, optionally at least one crosslinker and optionally further components.

It is preferred to employ at least one water-dispersible crosslinker. This may take the form in particular of a crosslinker which has free isocyanate groups. These may preferably take the form of isocyanurates which have free isocyanate groups, preferably isocyanurates which are derived from aliphatic, cycloaliphatic or aromatic diisocyanates having 4 to 12 carbon atoms. Examples include 1,6-hexamethylene diisocyanate, 1,12-dodecane diisocyanate, 2,2'- and 2,4'-dicyclohexylmethane diisocyanate or 2,4-tolyl diisocyanate. Preferred are isocyanurates based on 1,6-hexamethylene diisocyanate. Especially preferred are isocyanurates which have additional hydrophilic groups such as, in particular, polyethylene oxide groups. The preparation of such isocyanurates is known to the skilled worker. They are preferably employed as a solution in polar aprotic solvents such as, for example, ethylene carbonate or propylene carbonate. Further details on the preferred crosslinkers having isocyanate groups are disclosed in WO 2008/052913 page 34, line 6 to page 35, line 3. It is especially preferred to employ an isocyanurate which is based on 1,6-hexa-methylene diisocyanate (HMDI) and which has additional polyethylene oxide groups, the isocyanurate being dissolved in propylene carbonate (70% by weight of HMDI in propylene carbonate). The free isocyanate groups amount to approximately 11 to 12% by weight based on the solution. The crosslinker is preferably employed in an amount of from 1 to 10% by weight based on the amount of all solids of the formulation. The isocyanurate-based crosslinkers are suitable especially for crosslinking the copolymers I.

The formulation may furthermore comprise typical additives and adjuvants, UV stabilizers and colorants. Examples of such additives are mentioned in WO 2008/052913 page 35, line 17 to page 37, line 5.

Besides serving purely esthetic purposes, colorants and pigments may have a warning effect for example on birds or mammals, or may bring about a camouflage effect of the insecticide nets against insects. Moreover, dark colors may bring about shading, which may be desired, and may reduce the harmful effect of UV light on active ingredients and textile fibers when used in the open.

Crosslinkers and thickeners may be employed to enable uniform coating with the liquor in substrates which can only be wetted with difficulty, and therefore inhomogeneously, such as, for example, polyolefin fibers. For this purpose, it would also be possible to employ water-miscible solvents, which, however, is not preferred due to the harmful effect on the environment. A person skilled in the art is familiar with the adjuvants which are conventionally used and with their concentrations.

The formulations may preferably comprise antioxidants, peroxide scavengers, UV absorbers and light stabilizers. This is particularly recommended in the case of nets which are exposed to increased UV irradiation in the open or in greenhouses. The abovementioned additives protect not only the substrate fibers, but also the active ingredients, from decomposition due to radiation.

Suitable UV absorbers are described for example in WO 02/46503 or in WO 2007/077101. UV absorbers may firstly be used as a component in the formulation for finishing; secondly, they may also be incorporated as early as during the production of the fibers, for example in the case of polyolefins and polyesters. It is also possible advantageously to employ mixtures of a plurality of stabilizers which have different protective effects. As a rule, from 0.2 to 5% by weight, preferably from 0.25 to 4% and very especially preferably from 0.5 to 3.5% by weight of stabilizer is employed based on the weight of the untreated net. The amount in the formulation will be adjusted by the skilled worker to suit the task in hand.

Impregnating Method

To produce the coated nets according to the invention, the nonimpregnated nets are treated with a mixture comprising at least one polymeric binder and at least one insecticide, preferably with the abovementioned aqueous formulation. The treatment can be carried out by a method known to the skilled worker, for example by immersing or spraying the untreated net with the formulation. The treatment may be carried out at room temperature or else at elevated temperatures. If crosslinking is to be carried out, the treatment step at low temperatures, for example at from 10 to 70° C., may be followed by an aftertreatment at elevated temperatures, for example at from 50 to 170° C., preferably from 70 to 150° C.

Details of the treatment are disclosed for example in WO 2005/064072 page 29, line 16 to page 35, line 36.

Impregnating can be carried out by means of conventional impregnating apparatuses which are known to the skilled worker; however, impregnating can also be carried out by the end consumer themself by using simple means, for example by simply dipping, followed by drying in the air. To this end, it is preferred to select a suitable binder system which does not need curing of elevated temperatures. For example, the abovementioned copolymer II may preferably be employed for this purpose.

The amount of insecticides on the net is determined by a person skilled in the art according to the properties desired for the net. An amount of 30 to 300 mg/m$^2$ will be found advantageous, although the invention shall not be restricted to this range. An amount of 50 to 250 mg/m$^2$ may be preferably used.

The amount can be controlled by a person skilled in the art by first determining the amount of aqueous formulation taken up by the net in the course of the process, for example, depending on the process used, the amount after simply dipping or the amount after dipping and squeezing off, by weighing before and after. The amount taken up depends typically on the nature of the net used. Then, the concentration of the components, of which the insecticide is one, of the formulation is chosen such that the desired amount per unit area of net is obtained.

Properties and Use of the Nets According to the Invention

While the nets according to the invention provide good protection even from small insects, they still display a good permeability to air, water vapor and light.

Surprisingly, it has been found that, following impregnation, even insects which, in theory, should be able to pass through an impregnated net with a height $h_a$ can in fact no longer pass through the net. Therefore, it is possible to select a net with a greater height $h_a$ than would have been necessary without impregnation and, accordingly, the permeability to air, water vapor and light is better.

The nets according to the invention can be used as a protection from insect pests of all types. In particular, they may be employed as a protection from insects with a critical insect diameter from approximately 0.2 to approximately 0.6 mm, such as, for example, thrips, whiteflies or sand flies such as, for example, *Phlebotomus papatasi*.

The nets according to the invention can be used for protecting goods against pests. This at least minimizes the risk of the protected good becoming contaminated with pests. The goods to be protected may be, for example, wood stacks, fruit, vegetables, cereals, cocoa beans, coffee beans, tobacco or spices. The goods may further be goods which are stored or transported open, or goods which are stored or transported in the form of bales, packaging such as for example cardboard packaging or wood packaging. They can be employed, for example, by the goods to be protected—whether packed or unpacked—being wrapped in the nets.

In one preferred embodiment of the invention, the nets according to the invention can be used for the protection of tobacco. This protection of tobacco can extend to all stages of tobacco processing, tobacco storage or tobacco transportation. Here the nets can be used particularly for protecting against tobacco beetles (*Lasioderma serricorne*).

The nets according to the invention can be used for example for protecting dried or undried tobacco leaves, packaged tobacco or tobacco products. The form of protection depends on the particular product to be protected. Tobacco to be transported is typically packed in suitable packages, in particular cardboard boxes or drums. To achieve protection during storage and transportation, the tobacco-filled packages can be for example wrapped in the nets according to the invention. This can be done one at a time, or it is also possible for two or more packages, for example stacked cartons, to be wrapped together in or covered together with the nets. Apparatus such as shelves for example in which tobacco leaves are dried and/or fermented can be for example draped with the nets according to the invention, or additional props can be used to erect a tent above said apparatus. Tobacco products to be protected can be particularly cigars or cigarettes.

The nets according to the invention can furthermore be used for the protection of plants of any type, for example for the protection of useful plants or ornamentals. This may be done by covering the plants with the net. If the plants themselves are stable enough such as, for example, trees, they can be covered directly with the nets. If the plants are less stable such as, for example, seedlings, the net can be fixed above the plants with the aid of suitable supports. Suitable supports are simple posts or else arches as are customary for example for polytunnels.

It is especially advantageous that the nets can also be irrigated. Firstly, their permeability to water is sufficiently high that water will still reach the plants covered with the net, despite the close mesh of the latter, but, on the other hand, rot, which is caused by water lagging, is avoided. Furthermore, the insecticide still remains fixed on the net owing to the coating according to the invention, in particular a crosslinked coating, so that the activity of the net will be retained for a long time.

The nets according to the invention can furthermore be used as a material for the protection of window and door openings, for example as a material for windows or for doors intended for buildings such as houses, including animal houses, or else for tents. They can furthermore be used for the construction of greenhouses, for example again as material for windows or doors, or else as entire walls.

The insect protection nets may also be employed for the construction of fences as a protection from low-flying insects. Details on the construction of such fences are disclosed for example in EP 1 411 764 B1.

The examples which follow illustrate the invention:

A) Preparation of Nets Used:

The tests are carried out using three different nets each having rectangular meshes in the shape of a parallelogram:

|  | $h_a$ | b | Area [mm$^2$] | Thickness of fibers [mm] |
|---|---|---|---|---|
| Net 1 | 2 mm | 2 mm | 4 | |
| Net 2 | 1 mm | 1 mm | 1 | |
| Net 3 | 0.7 mm | 0.9 mm | 0.63 | 0.2 to 0.3 |

The nets each used for the tests are impregnated with an aqueous formulation comprising the insecticide alphacypermethrin, a thermally crosslinkable binder (about 81% of butyl acrylate, 16% of acrylonitrile, 2% of N-methylol(meth)acrylamide, 1% of acrylic acid) and also an isocyanate-based crosslinker, dried and crosslinked at about 100° C. for 1 min. Production details of the binder to be used and also of the impregnation are set out in WO 2005/064072 page 42 to page 50; the formulation used was of composition B01 (page 49, table 2). The amount of insecticide on the net is about 200 mg/m$^2$. It is controlled by determining the wet pick-up of the net (if appropriate, after squeeze-off under defined conditions) and adjusting the concentration of the formulation such that the desired amount per m$^2$ is obtained on the net.

B) Testing the Nets

B1) Testing of Effect Against Tobacco Beetle (*Lasioderma serricorne*)

The test apparatus used is a commercially available tube of cardboard (about 450 mm in length, 76 mm in diameter; 45 cm² in cross-sectional area). One end of the tube is sealed with the net to be tested, which is fixed with an adhesive tape. The other end of the tube has a commercially available, detachable cap closure. A tin of a transparent plastic material is adhered by means of adhesive tape, to the net-sealed end. The tin contains roasted oat flakes as feedstuff.

To perform the tests, the tube is placed upright, a specific number of beetles is inserted into the tube through the closable end for each test, and the tube is subsequently reclosed. The beetles try to get to the foodstuff through the net. How many beetles perish and how many are able to penetrate through to the feedstuff is determined at set times. Each test is carried out in 8 replications, the results of which are averaged.

A first series of tests used 10 cigarette beetles at a time. Table 1 below shows the mortality:

TABLE 1

Averaged mortality after one day and after two days

|  | Area | 1 day | 2 days |
|---|---|---|---|
| No net | — | 3% | 3% |
| Net 1 untreated | 4 mm² | 0% | 0% |
| Net 3 untreated | 0.63 mm² | 0% | 0% |
| Net 1 treated | 4 mm² | 100% | 100% |
| Net 3 treated | 0.63 mm² | 100% | 100% |

A second series of tests is carried out to investigate the influence of population density on net penetration within one day. One test series is carried out with 10 beetles and one with 20 beetles. Table 2 reports the proportions which pass through the net within one day irrespectively of whether the beetles perish after having passed through the net or not.

TABLE 2

Averaged penetration of net by beetles within one day.

|  | Area | 10 beetles | 20 beetles |
|---|---|---|---|
| Net 1 treated | 4 mm² | 95% | 100% |
| Net 2 treated | 1 mm² | 0% | 25% |
| Net 3 treated | 0.63 mm² | 0% | 0% |

The tests show that population pressure has a significant influence on net penetration rate. A coarse-meshed net can be penetrated by tobacco beetles despite impregnation. A 1 mm² net offers adequate protection at low population pressures, but becomes increasingly permeable at higher population pressures. Only inventive net 3 offers adequate protection at high population pressures.

B2) Testing of Effect Against Sand Flies (*Phlebotomus papatasi*)

The experimental set-up for the tests with sand flies consists of two cylindrical test chambers, one made of metal and one made of Plexiglas. A slider between the two chambers makes it possible to open and close the connection between the two chambers. A net can also be installed in the connection between the two chambers (net area: about 100 cm²).

About 12 h before each test, about 20 sand flies are placed in the steel chamber, the steel chamber ("sand fly chamber") is closed again, and the flies are made to fast until the start of the actual test. Immediately before commencement of the test, an anesthetized mouse is placed in the Plexiglas chamber ("mouse chamber") and the slider between the chambers is opened. After the slider has been opened, the sand flies try to penetrate through the net to the mouse and land thereon. Test duration is 30 min for each replication. Thereafter, the flies are sucked out of the chambers and the number of flies in each of the chambers is counted. A determination is also carried out as to whether the sand flies are still healthy; have been knocked down onto their backs at the end of the test; or are dead within 24 h. The tests are each replicated 7 times and averaged. The results are summarized in the tables which follow.

A comparative test is also carried out without net, as well as tests with treated net 3 and with untreated net 3. To simulate net damage, 3 holes each 3 mm in diameter are die cut into an untreated net 3 and also into a treated net 3 and the holed nets are identically installed in the apparatus for testing. The results are summarized in tables 3 and 4.

TABLE 3

Location of sand flies at end of test

|  | Sand fly chamber | Mouse chamber |
|---|---|---|
| No net | 11 | 8 |
| Net 3 untreated | 18 | >1 |
| Net 3 untreated, with holes | 12 | 7 |
| Net 3 treated | 19 | 0 |
| Net 3 treated, with holes | 19 | 0 |

TABLE 4

Averaged knock-down and mortality rates in sand fly chamber

|  | Knock-down after test | Mortality plus knock-down after 24 h |
|---|---|---|
| Net 3 untreated | 1% | 1% |
| Net 3 treated | 24% | 31% |

The tests show that a just 30-minute stay in the apparatus is sufficient to kill a major proportion of the sand flies.

Penetration of net 3 by sand flies is very low for an intact net even without impregnation, but penetration prevention can still be somewhat improved by impregnation. If, however, the net has holes, flies are able to pass through the net when it is untreated. Impregnation prevents flies passing through the holed net.

The explanation for this is that the flies will land even on a net with holes, and will first spend some time running around on the net before they "find" the hole in the net. These contact times are sufficient in the test to at least paralyze ("knock-down") the sand flies.

We claim:

1. An insect protection net made of textile fibers, the textile fibers having a thickness of 0.12 mm to 0.35 mm, and the textile fibers being arranged in such a way that the net comprises a pattern of meshes with an even number of corners, wherein the meshes represent an open area of the insect protection net, and the net being finished with at least one insecticide, wherein the meshes are selected from the group consisting of tetragonal meshes in the form of a parallelogram with the sides a and b and a height $h_a$, the height $h_a$ being from 0.25 mm to 0.7 mm and a length/height ratio $b/h_a$ of 1.3:1, and hexagonal meshes, which have three pairs of sides a, b and c which are in each case parallel to one another spaced apart by the distances $h_a$, $h_b$ and $h_c$, the height $h_a$ being from 0.25 mm to 0.7 mm and the ratio $((h_b+h_c)/2)/h_a$ being 1:1 to 5:1, octagonal meshes, which have four pairs of sides a, b, c and d which are in each case parallel to one another spaced apart by the distances $h_a$, $h_b$, $h_c$ and $h_d$, the height $h_a$ being from 0.25 mm to 0.7 mm and the ratio $((h_b+h_c+h_d)/3)/h_a$ being from 1:1 to 5:1, and the specifications of length and height referring in each case to the dimensions of a screen hole, and wherein the net is impregnated with a formulation comprising the at least one insecticide and at least one polymeric binder, wherein the polymeric binder is crosslinked, the crosslinking being carried out by means of isocyanurates which have free isocyanate groups.

2. The insect protection net according to claim 1, wherein the textile fiber is a polyolefin fiber or a polyester fiber.

3. The insect protection net according to claim 1, wherein the polymeric binder comprises at least the following monomers:

(A) from 50 to 95% by weight of at least one (meth)acrylate (A) of the general formula $H_2C=CHR^1-COOR^2$, where $R^1$ is H or methyl and $R^2$ is an aliphatic, linear or branched hydrocarbon radical having 1 to 12 carbon atoms, (B) from 1 to 20% by weight of (meth)acrylic acid and/or (meth)acrylic acid derivatives (B) which have additional functional groups, and (C) from 0 to 30% by weight of further, ethylenically unsaturated monomers other than the above.

4. The insect protection net according to claim 1, wherein the polymeric binder comprises at least the following monomers:

(A) from 60 to 95% by weight of ethylene, (B) from 5 to 40% by weight of at least one ethylenically unsaturated carboxylic acid selected from the group consisting of $C_3$- to $C_{10}$-monocarboxylic acids and $C_4$- to $C_{10}$-dicarboxylic acids, and (C) optionally from 0 to 30% by weight of further, ethylenically unsaturated monomers other than the above.

* * * * *